United States Patent
Cho et al.

(10) Patent No.: US 9,699,894 B2
(45) Date of Patent: Jul. 4, 2017

(54) DEFORMATION SENSING FLEXIBLE SUBSTRATE USING PATTERN FORMED OF CONDUCTIVE MATERIAL

(71) Applicant: Seoul National University R&DB Foundation, Seoul (KR)

(72) Inventors: Maenghyo Cho, Seoul (KR); Kyu Jin Cho, Seoul (KR); Junghyun Ryu, Seoul (KR); Je Sung Koh, Seoul (KR); Jong Gu Lee, Seoul (KR)

(73) Assignee: Seoul National University R&DB Foundation, Seoul (KR)

( * ) Notice: Subject to any disclaimer, the term of this patent is extended or adjusted under 35 U.S.C. 154(b) by 0 days.

(21) Appl. No.: 14/895,944

(22) PCT Filed: Mar. 11, 2015

(86) PCT No.: PCT/KR2015/002376
§ 371 (c)(1),
(2) Date: Dec. 4, 2015

(87) PCT Pub. No.: WO2016/143925
PCT Pub. Date: Sep. 15, 2016

(65) Prior Publication Data
US 2017/0048965 A1 Feb. 16, 2017

(51) Int. Cl.
*G01R 27/08* (2006.01)
*H05K 1/02* (2006.01)
(Continued)

(52) U.S. Cl.
CPC ............... *H05K 1/028* (2013.01); *G01B 7/20* (2013.01); *G01R 27/08* (2013.01); *H05K 1/02* (2013.01);
(Continued)

(58) Field of Classification Search
CPC ........ H05K 1/0277; H05K 1/028; H05K 1/00; H05K 1/02; H05K 3/00; H05K 3/10;
(Continued)

(56) References Cited

U.S. PATENT DOCUMENTS 5,047,952 A 9/1991 Kramer et al.
6,034,526 A * 3/2000 Montant ................ G01B 7/023
128/845

(Continued)

FOREIGN PATENT DOCUMENTS

JP H06-349650 A 12/1994
JP 2008-107514 A 5/2008
(Continued)

OTHER PUBLICATIONS

International Search Report issued in corresponding application No. PCT/KR2015/002376 mailed Nov. 27, 2015 (2 pages).

*Primary Examiner* — Hoai-An D Nguyen
(74) *Attorney, Agent, or Firm* — Osha Liang LLP

(57) ABSTRACT

Disclosed herein is a deformation sensing flexible substrate using a pattern formed of a conductive material. The deformation sensing flexible substrate, using the pattern formed of the conductive material, includes a flexible substrate; and conductive patterns in which conductors including a conductive material are arranged and formed to be contactable and non-contact to each other based on deformation of the flexible substrate.

6 Claims, 4 Drawing Sheets

(51) Int. Cl.
*H05K 3/12* (2006.01)
*G01B 7/16* (2006.01)
*G01R 27/02* (2006.01)
*G01N 27/00* (2006.01)
*G01R 27/00* (2006.01)
*G01N 27/02* (2006.01)

(52) U.S. Cl.
CPC .............. *H05K 3/12* (2013.01); *G01N 27/00* (2013.01); *G01N 27/02* (2013.01); *G01R 27/00* (2013.01); *G01R 27/02* (2013.01); *H05K 2201/07* (2013.01)

(58) Field of Classification Search
CPC ........ H05K 3/12; H05K 2201/07; G01B 7/02; G01B 7/023; G01B 7/026; G01B 7/04; G01B 7/042; G01B 7/16; G01B 7/18; G01B 7/20; G01B 5/30; G01B 9/02095; G01B 13/24; G01B 21/32
USPC .................. 324/600, 649, 691, 693, 699

See application file for complete search history.

(56) References Cited

U.S. PATENT DOCUMENTS

| | | | | |
|---|---|---|---|---|
| 6,370,964 | B1* | 4/2002 | Chang | ............... G01B 5/30 73/862.046 |
| 2006/0122528 | A1* | 6/2006 | Gal | ............... A61B 5/1135 600/534 |
| 2011/0005090 | A1* | 1/2011 | Lee | ............... G01D 5/145 33/1 PT |
| 2012/0256720 | A1* | 10/2012 | Byun | ............... H01C 10/10 338/2 |
| 2014/0035603 | A1* | 2/2014 | Ray | ............... G01L 1/205 324/693 |
| 2014/0042406 | A1* | 2/2014 | Degner | ............... H01L 27/326 257/40 |
| 2015/0109006 | A1* | 4/2015 | Choi | ............... B25J 13/084 324/691 |
| 2015/0128728 | A1* | 5/2015 | Salo | ............... G01L 1/04 73/862.626 |
| 2016/0377493 | A1* | 12/2016 | Hong | ............... G01L 1/205 73/774 |

FOREIGN PATENT DOCUMENTS

| | | |
|---|---|---|
| KR | 10-2009-0092982 A | 9/2009 |
| KR | 10-2012-0114961 A | 10/2012 |
| KR | 10-1504695 B1 | 3/2015 |

* cited by examiner

DEFORMATION SENSING FLEXIBLE SUBSTRATE USING PATTERN FORMED OF CONDUCTIVE MATERIAL

TECHNICAL FIELD

The present invention relates to a flexible substrate capable of sensing deformation, and more particularly, to a deformation sensing flexible substrate using a pattern of a conductive material which is capable of sensing minute or large deformation through sensing a change of conductivity by forming a conductive pattern including a conductive material on a flexible substrate so as to change conductivity according to deformation of an exterior thereof.

BACKGROUND ART

Various devices capable of sensing deformation of an object caused by an external force are disclosed. For example, a strain gauge is attached on a surface of the object and used in order to sense a state and an amount of deformation of the object, and senses the deformation thereof using a change of an electric resistance generated by shrinkage of a cross-sectional area and elongation of a length in a tension direction when the object is deformed.

The devices capable of sensing the deformation of the object are applied to various industrial fields, for example, "communication system for deaf, deaf-blind, or non-vocal individuals using instrumented glove" of U.S. Pat. No. 5,047,952 discloses a strain gauge attached to a hand glove, and/or the like to sense movement of a hand such as a finger and/or the like.

Besides, other devices configured to sense and control movement or deformation of an object are utilized in various industrial fields, and the present invention is developed by intension of not providing a conventional method of sensing deformation based on a deformation of the conductive material itself but a deformation sensing flexible substrate capable of sensing deformation in a simple method by forming a pattern including a conductive material on a flexible substrate and sensing conductivity by a contact between conductive materials.

DISCLOSURE

Technical Problem

The present invention is directed to a deformation sensing flexible substrate using a pattern of a conductive material which is capable of sensing a deformation through sensing a change of conductivity in response to contact between corresponding conductive materials by exterior deformation by forming a conductive pattern including a conductive material on a bendable or foldable flexible substrate.

Technical Solution

One aspect of the present invention provides a deformation sensing flexible substrate using a pattern formed of a conductive material which includes a flexible substrate; and conductive patterns including conductors having a conductive material arranged on a surface of the flexible substrate.

According to the present invention, the conductive patterns may include the plurality of conductors formed to extend in a longitudinal direction on the surface of the flexible substrate, and the conductors may have separation spaces set in a width direction and be spaced apart from each other in the width direction.

According to the present invention, the conductor may be formed on the surface of the flexible substrate in a reverse trapezoidal shape in which a width is increased toward an upper portion.

According to the present invention, the conductors each formed to extend in the longitudinal direction may include a plurality of block typed conductors arranged to have separation spaces in the longitudinal direction, and separation spaces between the block typed conductors forming upper conductors may be disposed on a straight line in the width direction of separation spaces between the block typed conductors forming lower conductors.

According to the present invention, surfaces of the block typed conductors which face each other in the longitudinal direction may be inclined, and formed to protrude toward the facing surface as proceed from the surface of the flexible substrate toward upper portions thereof.

According to the present invention, the conductive patterns including the conductors may be formed on both surfaces of the flexible substrate.

According to the present invention, the flexible substrate may include a first area and a second area which is formed to be foldable along a folding line L with respect to the first area 24, and conductive patterns formed in the first area include first conductors extending in the longitudinal direction and are spaced apart from each other with respect to the width direction and arranged in plural numbers, and spaces between the first conductors spaced in the width direction form second conductor receiving parts, and conductive patterns formed in the second area may include second conductors each formed to extend in the longitudinal direction, and the second conductors may be spaced apart from each other by widths of the first conductors in a direction crossing the longitudinal direction and arranged in plural numbers, and thus, when the second area is folded with respect to the first area, the second conductors may be inserted into second conductor receiving parts between the first conductors, and the first conductors are contact with the second conductors.

Advantageous Effects

According to the present invention, the conductive pattern is formed of conductors including a conductive material on the flexible substrate which is foldable or bendable by an external force, and when a contact between corresponding conductive materials is generated by the exterior deformation, a change of the conductivity by the above is sensed and the deformation can be sensed.

Using the change of the conductive by the contact between the conductors, existence of the deformation of the object applied by the deformation sensing substrate and minute and large deformation may be sensed.

When the present invention is applied for sensing bending deformation caused by an external force, the bending can be sensed only by a current flow through the conductors forming the conductive pattern, and thus, a circuit structure and a compensation device can be omitted or simplified, and a simpler and more precise device for sensing the bending can be realized.

Also, according to the present invention, since the current flow is possible in a bending state by a simpler structure, a function as a power controller for controlling a specific operation can be served as well as detection of the bending deformation.

BEST MODE OF THE INVENTION

Hereinafter, the embodiments of the present invention will be described in detail with reference to accompanying drawings.

Figure 1:
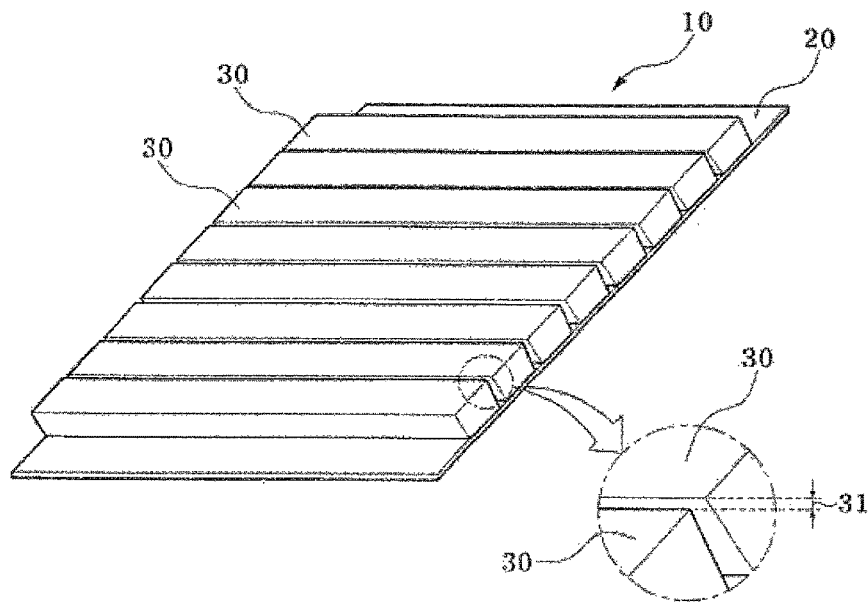
FIG. 1 is a view illustrating a deformation sensing flexible substrate using a pattern formed of a conductive material according to an embodiment of the present invention.
Figure 2:
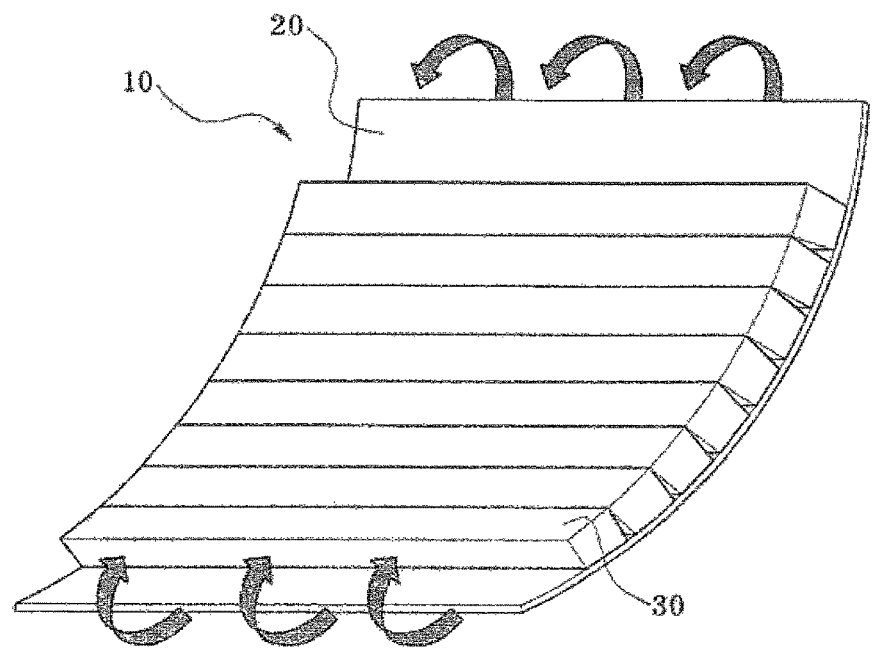
FIG. 2 is a view illustrating a bending deformation embodiment of the deformation sensing flexible substrate using the pattern formed of the conductive material of FIG. 1.

FIG. 1 is a view illustrating a deformation sensing flexible substrate using a pattern formed of a conductive material according to an embodiment of the present invention, and FIG. 2 is a view illustrating a bending deformation embodiment of the deformation sensing flexible substrate using the pattern formed of the conductive material of FIG. 1.

Referring to the above drawings, a deformation sensing flexible substrate 10 using a pattern formed of a conductive material according to the embodiment of the present invention includes a flexible substrate 20 and conductive patterns including a conductive material formed on a surface of the flexible substrate 20.

According to the embodiment of the present invention, the conductive patterns are patterned so that conductors 30 formed of a conductive material on the surface of the flexible substrate 20 are contactable and non-contact to each other based on deformation of the flexible substrate 20, and thus, the conductive patterns are formed to sense deformation of the flexible substrate 20 such as bending, folding, and/or the like.

Referring to the embodiment of the present invention described with reference to FIG. 1, the conductive patterns include the conductors 30 formed to extend in a longitudinal direction on the surface of the flexible substrate 20 in a bar shape, and each conductor 30 has a separation space 31 set in a width direction, and the conductors 30 are spaced apart from each other and arranged. That is, one of the conductors 30 in a bar shape formed to extend in the longitudinal direction is disposed on an upper end in the width direction, and another conductor 30 is spaced at a lower position in the width direction by the separation space 31 and formed, and also, the other conductor 30 is spaced at a lower position in the width direction by the separation space 31 and formed. The separation space 31 is set based on an amount of a bending deformation to be sensed. For example, when the separation space 31 is small, a minute bending deformation may be sensed as a deformation, and when the separation space 31 is increased, the amount of the deformation to be sensed is increased. In another example, the separation spaces 31 are constant, and the bending deformation may be determined from a predetermined time point based on a change of conductivity between the conductors forming the conductive patterns.

According to the embodiment of the present invention, the conductor 30 is formed on the surface of the flexible substrate 20 in a reverse trapezoidal shape in which a width is increased toward an upper portion. Thus, a decrease of an attached area between the conductor 30 and the flexible substrate 20 is possible, and thus, the disturbance of the deformation of the flexible substrate 20 by the attached portion of the conductor 30 may be minimized.

A conductive material forming the conductor 30 may be deformed by an external force. Thus, when the conductors 30 are in contact with each other by deformation of the flexible substrate 20, a point contact or a line contact is formed in an initial stage of the bending, but the contact surfaces are deformed as the deformation is increased, and thus, the surface contact is generated.

According to an operation of the deformation sensing flexible substrate using the pattern formed of the conductive material according to the embodiment of the present invention, in a state shown in FIG. 1, the conductors 30 are spaced apart from each other, and thus, a current flow is not generated between the conductors 30.

However, as shown in FIG. 2, when a bending deformation of a surface on which the conductor 30 is attached in a concave direction is generated in the flexible substrate 20, a distance between the conductors 30 is decreased, and the separation space 31 disappears, and the conductors 30 are in contact with each other. Also, the contact is the line contact in the initial stage of the bending, and as the amount of the bending is increased, the contact becomes the surface contact. Different from the deformation of FIG. 2, when the deformation of the flexible substrate 20 is a twist deformation, a point contact is generated between the conductors 30 in a twist direction.

As the flexible substrate 20 deformed by the external force, the conductive pattern is changed from a conductor non-contact mode of the initial state into a conductor contact mode, and as the deformation of the flexible substrate 20 is increased, the contact area is also increased. Thus, the conductivity of the deformation sensing flexible substrate 10 is changed from a non-conductive state into a conductive state, and an amount of the conductivity is changed based on the amount of the bending deformation. Thus, when the change of the conductivity generated along the conductors 30 on the deformation sensing flexible substrate 10 is sensed, existence of deformation and the amount of the deformation may be sensed.

For example, when the deformation sensing flexible substrate according to the embodiment of the present invention is attached onto each joint portion of a human-computer interface device in a glove shape, movement of each joint can be precisely sensed. Also, the deformation sensing flexible substrate according to the embodiment of the present invention can be used in medical fields including a device guiding posture correction of a waist and/or the like and sport science fields such as pitching form correction. Also, the deformation sensing flexible substrate according to the embodiment of the present invention can be used in an airplane field such as monitoring an amount of repetitive bending of an airplane wing in real time and predicting a flight lifetime of an airplane, an/or the like. Thus, the deformation sensing flexible substrate according to the embodiment of the present invention can be applied to various devices requiring sensing deformation such as bending, twisting, and/or the like and controlling an operation based on an amount of deformation.

According to the embodiment of the present invention, the flexible substrate may also have conductivity, and in FIG. 1, the conductivity may be only caused by the flexible substrate and be in a low conductive state, and in FIG. 2, the conductivity may be caused by the bending deformation state through the flexible substrate and the conductive pattern and be in a high conductive state. Thus, the change of the conductivity of the deformation sensing flexible substrate 10 may be sensed and the existence of the deformation and the degree of the deformation may be sensed.

In FIGS. 1 and 2, the conductive pattern is formed on one surface of the flexible substrate 20, but the conductive patterns may be formed on the one surface and a surface opposite the one surface of the flexible substrate 20, respectively, and thus, the conductive patterns may be formed on both sides. When the conductive patterns are formed on the both sides of the flexible substrate, the conductivity is changed in a conductive pattern formed on one of the both surfaces based on a bending direction, and thus, the bending direction may also be sensed.

Figure 3:
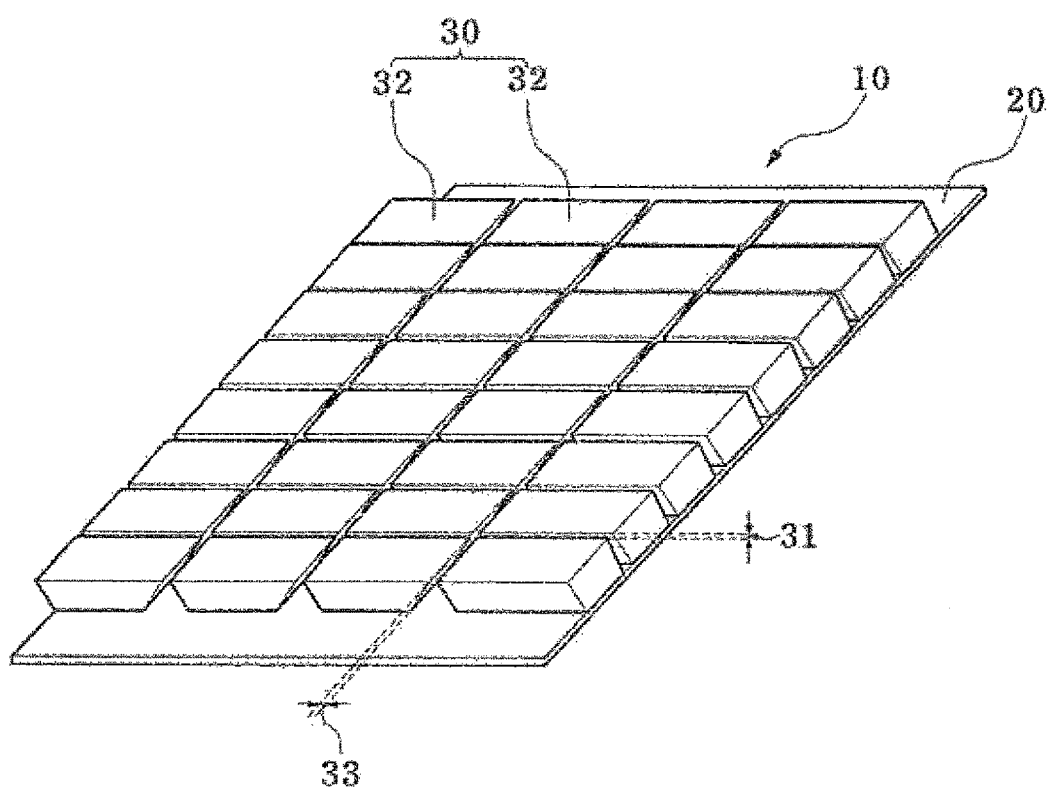
FIG. 3 is a view illustrating a deformation sensing flexible substrate according to another embodiment of the present invention.

FIG. 3 is a view illustrating a deformation sensing flexible substrate 10 according to another embodiment of the present invention.

Referring to FIG. 3, a conductive pattern formed on a surface of a flexible substrate 20 includes conductors 30 formed to extend in a longitudinal direction which includes an assembly of a plurality of block typed conductors 32 arranged to have separation spaces 33. Thus, the conductive patterns include the plurality of block typed conductors 32 having separation spaces 31 and 33 in a width direction and the longitudinal direction and arranged. Here, separation spaces 33 are disposed between block typed conductors 32 in the longitudinal direction on a straight line. That is, separation spaces 33 between block typed conductors 32 forming upper side conductors are disposed on the straight line in the width direction with respect to separation spaces 33 between block typed conductors 32 forming lower side conductors. Also, surfaces of the block typed conductors 32 which face each other in the longitudinal direction are inclined and formed to protrude toward the facing surface as proceed from a surface of the flexible substrate 20 toward upper portions thereof.

According to the embodiment described in FIG. 3, the deformation sensing flexible substrate 10 may sense bending with respect to two directions. That is, with respect to the view shown in FIG. 3, when upper and lower sides are deformed by bending in directions closing each other, or left and right sides are deformed by bending in directions closing each other, the block typed conductors 32 forming the conductive patterns in the bending direction are in contact with each other to generate conductivity, and a contact area is changed based on an amount of the bending, and thus, the conductivity is changed, thereby being sensed.

Figure 4:
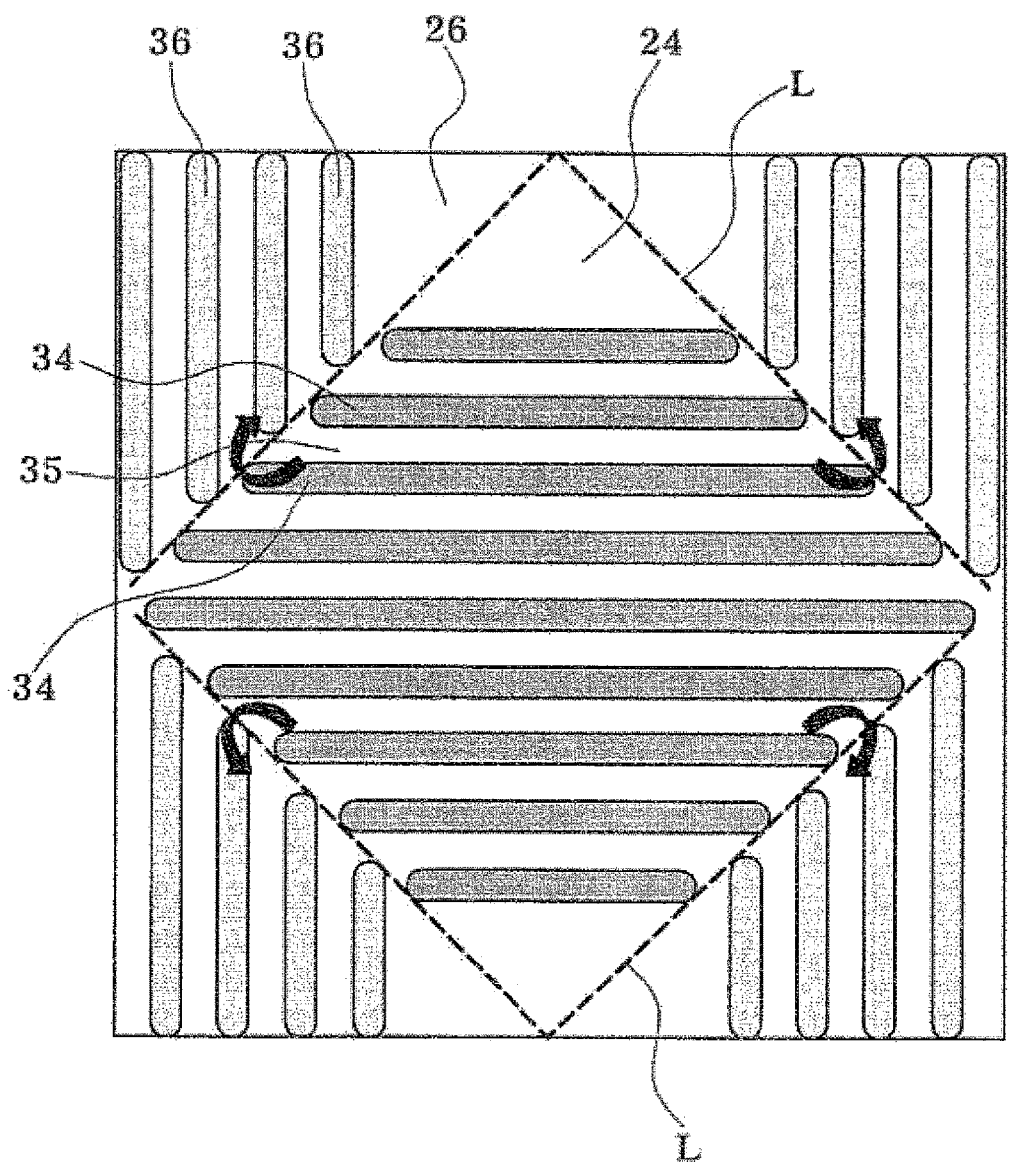
FIG. 4 is a view illustrating a deformation sensing flexible substrate using a pattern formed of a conductive material according to still another embodiment of the present invention in an unfold state of the deformation sensing flexible substrate.
Figure 5:
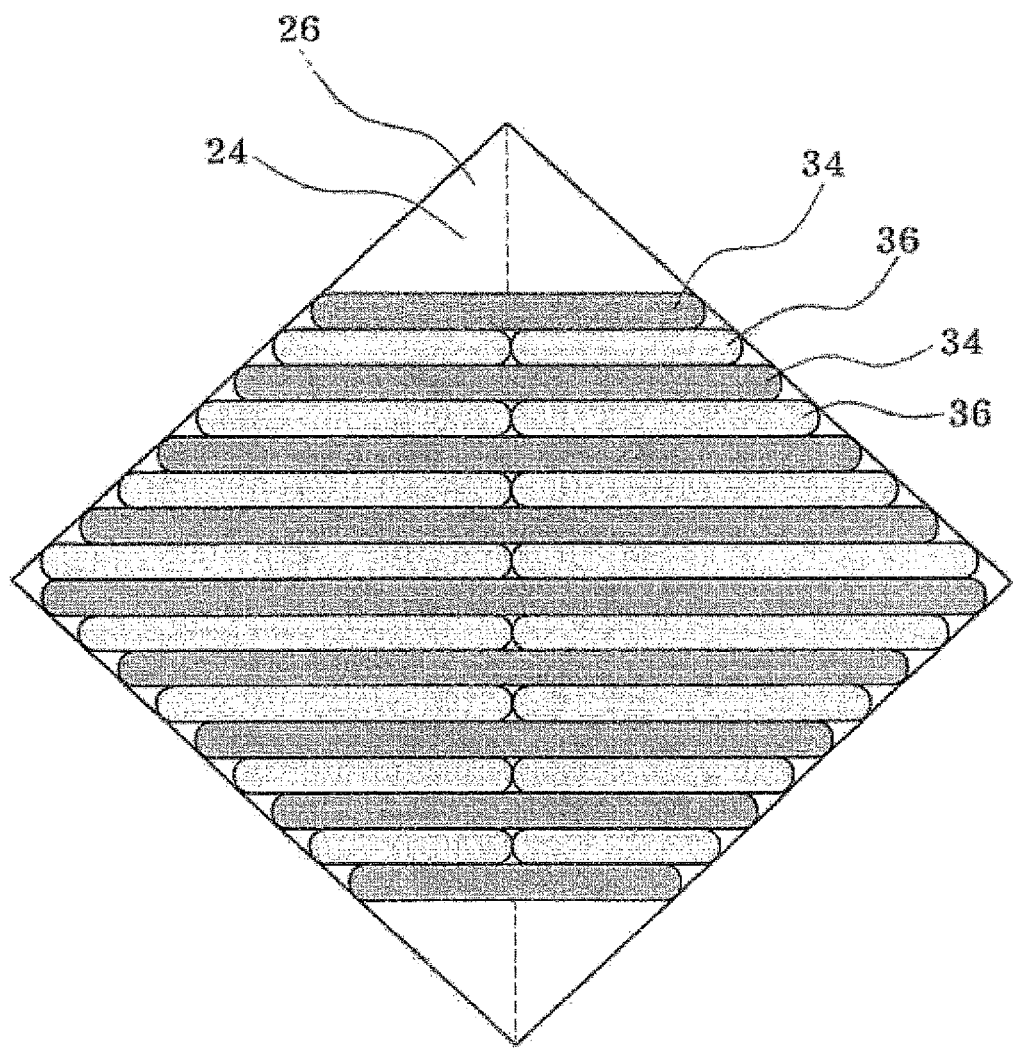
FIG. 5 is a view illustrating a fold state of the deformation sensing flexible substrate of FIG. 4.

FIGS. 4 and 5 are views illustrating a deformation sensing flexible substrate using a pattern formed of a conductive material according to still another embodiment of the present invention, and FIG. 4 is a view illustrating the deformation sensing flexible substrate in an unfold state, and FIG. 5 is a view illustrating the deformation sensing flexible substrate in a fold state. The deformation sensing flexible substrate according to the still another embodiment of the present invention described with reference to FIGS. 4 and 5 is an embodiment such as a flexible display to sense bending of an object having a plate shape which is bendable.

Referring to the drawings, the deformation sensing flexible substrate using the pattern formed of the conductive material according to the still another embodiment of the present invention includes a flexible substrate 20 having first and second areas 24 and 26 which are foldable with each other. That is, the flexible substrate 20 includes a first area 24 and a second area 26 which is formed to be foldable along a folding line L with respect to the first area 24.

Conductive patterns formed in the first area 24 include first conductors 34 extending in a longitudinal direction and are spaced apart from each other in a width direction and arranged in plural numbers, and spaces between the first conductors 34 spaced in the width direction form second conductor receiving parts 35.

Conductive patterns formed in the second area 26 are disposed in a shape extending in the longitudinal direction, and include second conductors 36 spaced apart from each other by widths of the first conductors 34 in a direction crossing the longitudinal direction and arranged in plural numbers. The second conductors 36 forming the conductive patterns in the second area 26 are parallel with second conductor receiving parts 35 in the first area while the flexible substrate 20 is in an unfold state and have sizes corresponding to the second conductor receiving parts 35.

As shown in FIG. 4, when the flexible substrate 20 is in the unfold state, the first conductors 34 and the second conductors 36 are arranged perpendicular to each other and maintain in a non-contact state with each other.

When the second areas 26 are folded with respect to the first areas 24 along the folding line L in the state shown in FIG. 4, the second conductors 36 are disposed between the first conductors 34 as shown in FIG. 5 and the flexible substrate 20 is folded.

Thus, in the unfold state shown in FIG. 4, conductivity is not formed between the first conductors 34 and the second conductors 36, but in the fold state shown in FIG. 5, the first conductors 34 and the second conductors 36 are in contact with each other, and thus, the conductivity is formed therebetween.

In a foldable flexible display, in order to control a screen displayed on the flexible display, the detection of whether the flexible display is in a fold state or an unfold state, that is, in a usage state or in a storage state, is necessary.

The deformation sensing flexible substrate applied to a flexible display using the pattern formed of the conductive material according to the still another embodiment described in FIGS. 4 and 5 may sense the existence of folding based on a change of conductivity in the unfold state and the fold state, thereby recognizing whether the flexible display is in the usage state or in the storage state. Also, the deformation sensing flexible substrate may serve as a power controller configured to apply power only in the unfold state. In the embodiment applied to the flexible display, the flexible substrate may be a portion of the flexible display, or an additional film attached to the flexible display.

It will be apparent to those skilled in the art that various modifications can be made to the above-described exemplary embodiments of the present invention without departing from the spirit or scope of the invention. Thus, it is intended that the present invention covers all such modifications provided they come within the scope of the appended claims and their equivalents.

The invention claimed is:

1. A deformation sensing flexible substrate using a pattern formed of a conductive material, comprising:
   a flexible substrate; and
   conductive patterns including a plurality of first conductors comprising a conductive material arranged on a surface of the flexible substrate,
   wherein the plurality of first conductors extend in a longitudinal direction and are spaced apart from each other with separation spaces in a width direction between the plurality of first conductors, and
   wherein upon bending deformation in the width direction, the separation spaces are narrowed and the plurality of first conductors are changed from a conductor non-contact mode into a conductor contact mode, and conductivity between the conductors is changed to sense the bending deformation.

2. The deformation sensing flexible substrate of claim 1, wherein the plurality of first conductors comprise a reverse trapezoidal shape in which a width is increased toward an upper portion.

3. The deformation sensing flexible substrate of claim 1, wherein the plurality of first conductors are formed on both surfaces of the flexible substrate.

4. The deformation sensing flexible substrate of claim 1, wherein the conductive patterns further include a plurality of second conductors comprising a conductive material arranged on a surface of the flexible substrate,
   wherein the plurality of second conductors extend in a width direction and are spaced apart from each other with separation spaces in a longitudinal direction between the plurality of second conductors, and
   wherein upon bending deformation in the longitudinal direction, the separation spaces are narrowed and the plurality of second conductors are changed from a conductor non-contact mode into a conductor contact mode, and conductivity between the conductors is changed to sense the bending deformation.

5. The deformation sensing flexible substrate of claim 4, wherein the plurality first and second conductors comprise a block shape.

6. The deformation sensing flexible substrate of claim 5, wherein surfaces of the block shape conductors which face each other in the longitudinal direction are inclined and protrude from the surface of the flexible substrate.

\* \* \* \* \*